United States Patent [19]

Borgen

[11] 4,050,448

[45] Sept. 27, 1977

[54] METHOD OF REVERSIBLE STERILIZATION

[76] Inventor: Jennings O. Borgen, 1100 University, Apt. 3J, Seattle, Wash. 98101

[21] Appl. No.: 708,552

[22] Filed: July 26, 1976

Related U.S. Application Data

[62] Division of Ser. No. 579,484, May 21, 1975.

[51] Int. Cl.² ............................................. A61F 5/00
[52] U.S. Cl. .................................. 128/1 R; 128/131; 3/1; 128/132 R
[58] Field of Search ................... 128/1 R, 131, 132 D; 3/1

[56] References Cited

U.S. PATENT DOCUMENTS

| 3,422,813 | 1/1969 | Braley | 128/1 R |
| 3,646,616 | 3/1972 | Keshin | 3/1 |

FOREIGN PATENT DOCUMENTS

| 813,297 | 9/1951 | Germany | 128/131 |

Primary Examiner—Jerome Schnall
Attorney, Agent, or Firm—Seed, Berry, Vernon & Baynham

[57] ABSTRACT

Method for reversible sterilization of females in which caps are placed over the fimbriated ends of the Fallopian tubes and sutured to the serosa. The caps block passage of sperm and ova to prevent pregnancy. The caps can be sutured to and removed from the ends of the Fallopian tubes without damage to the transport mechanism inside.

3 Claims, 5 Drawing Figures

FIG. 1
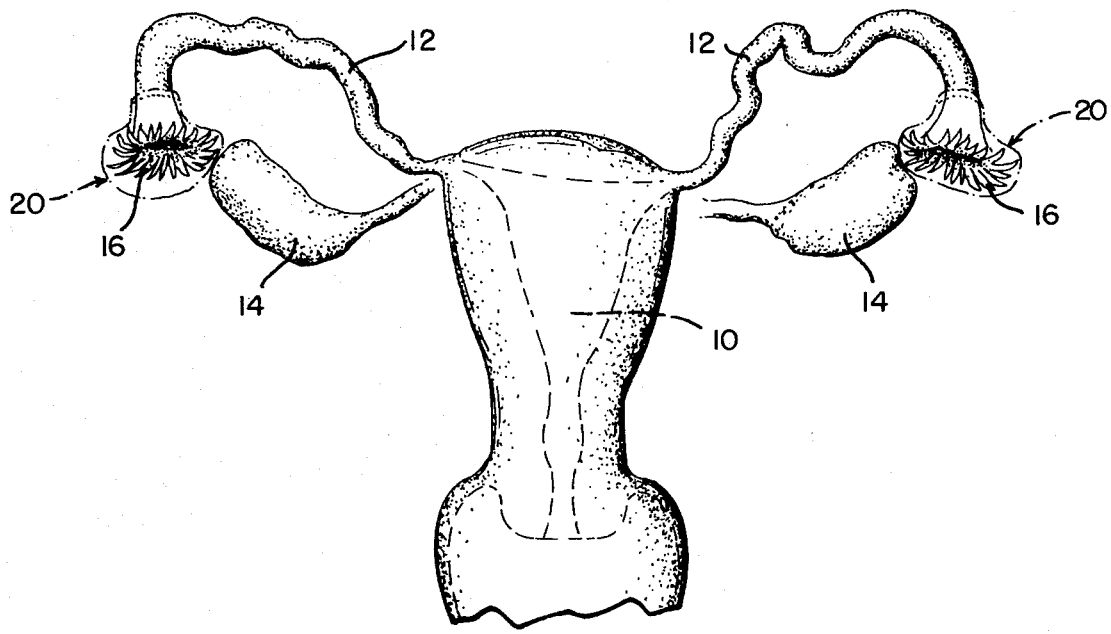
FIG. 2
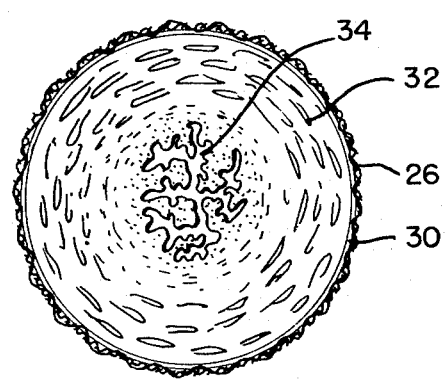
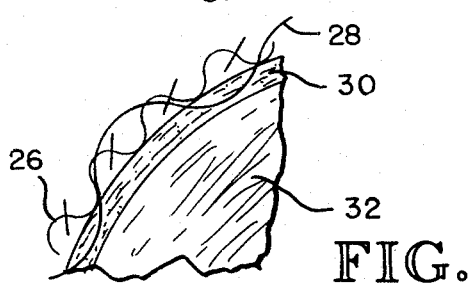
FIG. 3
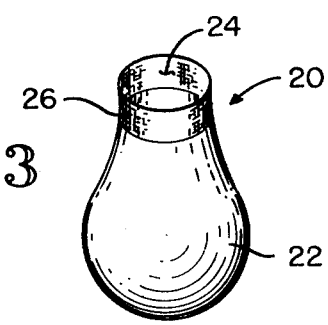
FIG. 4
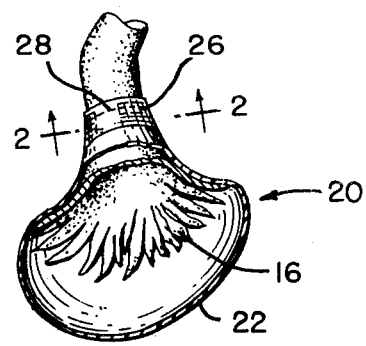
FIG. 5

METHOD OF REVERSIBLE STERILIZATION

This is a division of application Ser. No. 579,484, filed May 21, 1975 pending.

BACKGROUND OF INVENTION

The invention relates to a method for a surgical, reversible sterilization of females.

As is generally recognized, birth control has been relied upon as the principal means to control over-population in the world. In the field of birth control the prevention of conception is considerably more acceptable for controlling population growth than for females to submit themselves to abortion. However, the methods heretofore proposed for contraception have had inherent drawbacks which limit their applicability and effectiveness. Ideally, contraception should be 100% effective in preventing conception; it should not rely on will power and should not interfere with the sexual relationship; and it should be simple and low in cost. It should not have harmful, psychological side-effects. A very important feature of an ideal contraceptive method is that it be reversible so that it can be resorted to for family planning so that addition children may be had if desired.

Numerous techniques of contraception have been employed. Birth control pills for instance, have disadvantages and are controversial. Mechanical devices such as condoms, diaphragms and vaginal foams are awkward and unreliable. Additionally, surgical methods have included rings, clamps and plugs of various types. Also interuterine devices have fallen out of favor because of other disadvantages. Surgical techniques so far employed have had a common failing. They interfere with, block, or damage the transport mechanism of the Fallopian tubes. Stated another way, injury is caused to the celliated cells and/or to the muscular layer of the tube, or the surgical technique may effect complete separation of a portion of the tube. In addition, other techniques have been too complicated for the average operator in that they require sophisticated equipment either to install or attach a device, or to cut or coagulate the tube. These methods are not really reversible because of the injury they cause to the transport mechanism. It is not maintained that all of the techniques which purport to be reversible are not in fact so, but, injuries to those parts of the Fallopian tubes above identified are not usually reparable and therefore reduce the patient's chances of become pregnant again.

SUMMARY OF THE INVENTION

In accordance with this invention a method therefor is provided to obstruct the Fallopian tubes of the human female in a manner which does not injure the tube's internal transport capability. A cap device is placed over the fimbriated end of the Fallopian tube and sutured to the serosa. The cap material is an inert, soft thin walled, flexible, light, medical grade elastomeric material which may also be radio opaque. Suturing of the cap is confined to the serosa of the tube. The material is such that it will not cause tissue reaction or adhesions.

Accordingly, it is among the features and advantages of this invention to provide a method and for the reversible sterilization of females which is a relatively simple and inexpensive operative procedure. The invention satisfies a great need as well as being highly desirable by many. The procedure involves some post-operative discomfort to the patient that always associates with an incision in the stomach but is certainly less than the discomfort associated with a Caesarean section. The operation is not as major as an appendectomy. The procedure can be performed by most doctors who do surgery. The procedure provides a reliable method of reversible sterilization. The method of this invention offer an opportunity for a woman to change her mind about child bearing. It enables a woman, who may decide that she does not want to get pregnant, to avoid subjecting herself to permanent sterilization. The invention may be more acceptable to women who for one reason or another are disinclined to the use of pills, IUD's or other birth control methods and devices. The procedure does not interfere with perastolsis of the tube which is part of the tube transport capability. The cap can be surgically removed, restoring full, normal conception capability.

BRIEF DESCRIPTION OF DRAWING

FIG. 1 is an illustration partly in cross-section showing uterus, Fallopian tubes and ovaries and location of caps;

FIG. 2 is a typical cross-sectional view through a Fallopian tube to illustrate general details of its structure and to illustrate suturing of the cap to the outer layer or serosa of the tube;

FIG. 3 is a perspective view illustrating additional details of the cap; and

FIG. 4 is a further illustration, partially in cross-section showing a cap sutured into place over the fimbriated end of a Fallopian tube.

FIG. 5 is a cross-section showing a cap sutured to a Fallopian tube.

DESCRIPTION OF PREFERRED EMBODIMENT

The FIG. 1 represents the organs concerned including uterus 10, Fallopian tubes 12, ovaries 14 and the fimbriated Fallopian tube ends 16. The abdomen of the patient is opened with a small lower abdominal incision. Each individual tube is then brought up in turn to the incision. The caps, generally identified by the number 20, are made up of a solid portion 20 in the form of a round flat or oblong sack-like article which is generally large enough to surround and encase the tube fimbria while at the same time enabling some freedom of movement for the fimbria. The tube itself on an average is about ½ centimeter in diameter proximal to the fimbria. The solid cap portion 22 will be in the area of 2 to 2½ centimeters across and it will have an open end 24 approximately the size of the tube. It will be understood that the term "solid" as used herein embraces not only a continuous or solid thin wall but any satisfactory material which is impervious to the passage of sperm or ova. The cap opening 24 may be defined by a slightly tapering extension of portion 22 so that a piece can be cut off to match the suturing section size to the Fallopian tube. More preferably, however, the cap section 22 will have bonded or sealingly attached thereto a suturing section 26 of fine mesh also of an inert medical grade elastomeric material. It is not essential that cap portion 22 and suturing strip 26 be of the same material. Suturing portion 26 on the open end 24 of cap section 22 is to facilitate suturing. The solid cap portion 22 is an inert medical grade silicon elastomeric material such as silicon rubber, but which is also thin walled, flexible and preferably radio opaque. The material from which the cap is made, including the suturing strip 26, is the type of base material which would not cause tissue reaction or adhesions. It is contemplated that other medical grade plastic materials such as Dacron or Teflon can be used for both the cap and suturing strip.

As can be seen in FIGS. 2 and 5 after the individual tubes are brought up to the incision the caps are placed over the end of the fimbriated tube and secured to the serosa by sutures 28. The tube has outer layer or serosa 30, muscular layer 32 and tube interior which is generally open but lined with ciliated cells 34. Care is taken in placing the cap over the fimbriated end of the tube that the sutures do not enter the muscular layer 32. The ends of both tubes are thus capped and sutured as described. Fiberblastic proliferation will seal off the union or interface beween suturing section 26 of the cap and serosa. In this way, the small diameter sperm will be unable to pass through the cap or the serosa-cap interface.

What is claimed is:

1. The method of temporarily and reversibly obstructing and blocking the interior of the Fallopian tubes of a human female comprising the steps of:
  a. gaining access to the ends of the Fallopian tubes by lower abdominal incision,
  b. placing over the fimbriated end of each of the tubes a cap of inert, medical grade elastomeric material which is light and flexible, and
  c. suturing said cap to the serosa of the tube such that access to and egress from the end of the tube interior is prevented, and such that said cap and said suturing do not interfer with, damage or injure the sperm and ovum transport capability of the interior of the tubes.

2. A method of temporarily and reversibly capping the ends of the Fallopian tubes of a human female for reversible sterilization, comprising:
  gaining access to the ends of the Fallopian tubes by incision,
  capping the fimbriated ends of the Fallopian tubes with a cap of inert, medical grade, flexible, elastomeric material, and
  suturing the cap around the tubes so that the cap encloses the fimbriated end of the tubes and provides an impervious barrier to the passage of sperm and ova therethrough without interfering with the perastolsis action of the ciliated cells of the Fallopian tubes.

3. The method of claim 2 wherein the cap is sutured to the serosa around the outer circumference of the Fallopian tubes without the sutures entering the muscular layer of the tubes.

* * * * *